United States Patent

Straub et al.

[11] Patent Number: 4,590,936
[45] Date of Patent: May 27, 1986

[54] MICROSURGICAL INSTRUMENT

[75] Inventors: Reinhold Straub, Schramberg; Eugen Eberhard, Mülheim, both of Fed. Rep. of Germany

[73] Assignee: Ewald Hensler, Immendingen, Fed. Rep. of Germany

[21] Appl. No.: 575,865

[22] Filed: Feb. 1, 1984

[30] Foreign Application Priority Data

Feb. 2, 1983 [DE] Fed. Rep. of Germany ....... 3303349

[51] Int. Cl.$^4$ ............................................. A61B 17/32
[52] U.S. Cl. .................................................. 128/305
[58] Field of Search ................. 30/240, 29.5; 128/318, 128/305.1, 305, 312, 321, 319, 320, 303, 303 A

[56] References Cited

U.S. PATENT DOCUMENTS 2,387,633  10/1945  Alpert ..................................... 30/240
3,618,611  11/1971  Urban ..................................... 30/240
4,499,899   2/1985  Lyons ..................................... 128/305

Primary Examiner—Robert Peshock
Attorney, Agent, or Firm—Leonard Bloom

[57] ABSTRACT

A microsurgical instrument has a stationary jaw part that is connected via a tube with a stationary handle part, and also has a rotatable jaw part that is attached to a rotating rod supported in the tube. The rotating rod is caused to rotate by means of a helical inclined curve and a tappet in engagement therewith that is axially displaceable and secured against twisting. The tappet is displaced by means of a pivotable actuating handle part. In accordance with the invention, the inclined curve is embodied as a slit in a sleeve supported in the posterior end of the tube and is engaged by a radial pin of the tappet that is received coaxially in the sleeve. The stationary handle part and the actuating handle part are disposed substantially at right angles to the tube and embodied in scissor-like fashion. The posterior end of the tappet is attached to the free lever arm of the actuating handle part in a non-twisting and displaceable manner.

20 Claims, 2 Drawing Figures

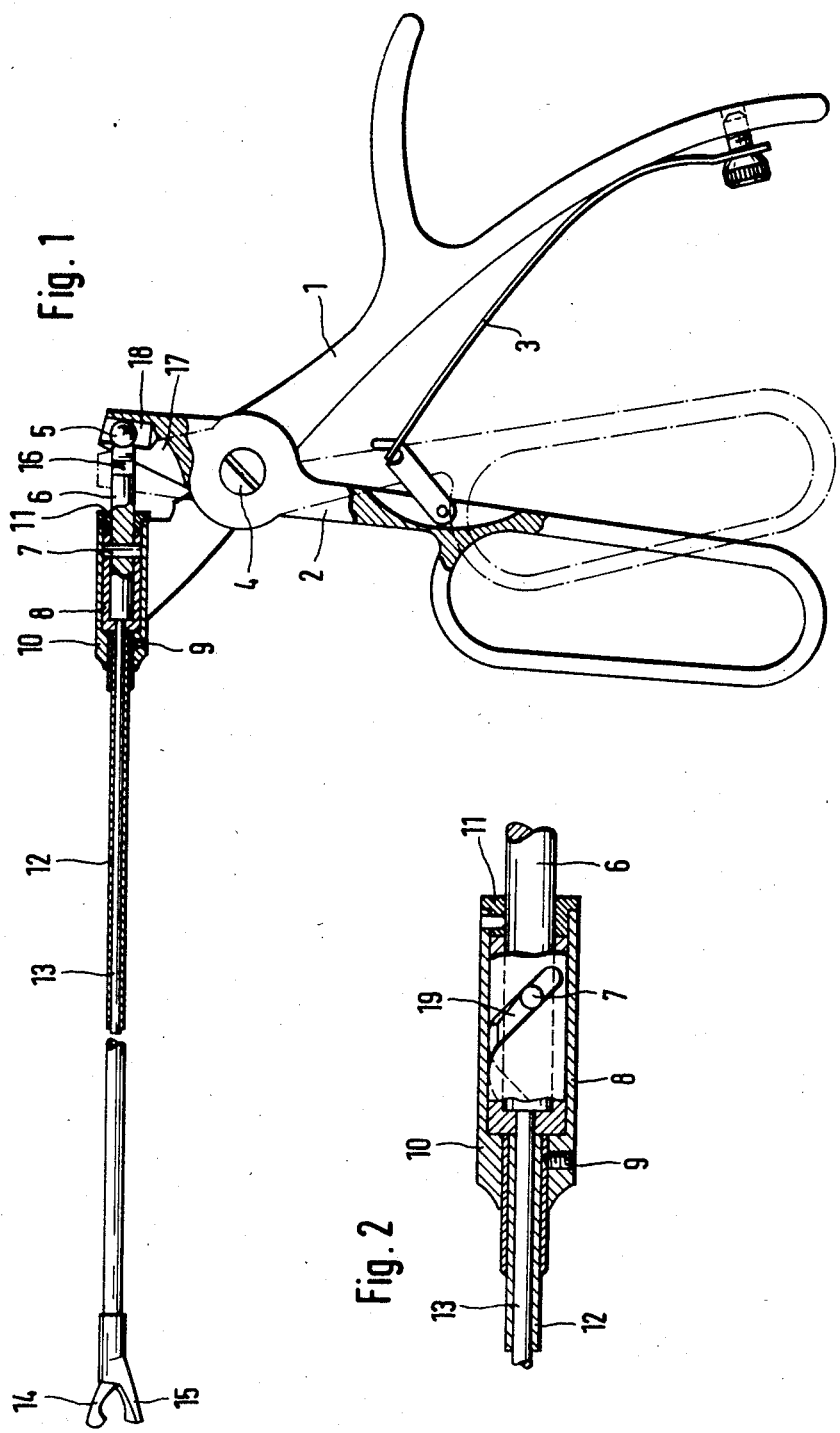

MICROSURGICAL INSTRUMENT

FIELD OF THE INVENTION

The present invention relates generally to a microsurgical instrument in which a stationary jaw part is connected via a tube with a stationary handle part, and another jaw part is rotatable toward the stationary jaw part. The rotatable jaw part is provided on a rotating rod that is supported coaxially and rotatably in the tube, and at its posterior end the rotating rod communicates with an axially continuous, helical inclined curve. A tappet engages this curve and is axially displaced in a non-twisting manner by an actuating handle part articulated on the stationary handle part.

BACKGROUND OF THE INVENTION

A microsurgical instrument of this type is known from U.S. Pat. No. 4,258,716. The essential features of such an instrument are the two jaw parts that are rotatable toward one another; depending upon the intended use, they may be embodied as grippers, scissors, clamps or the like. The jaw part of the instrument is also useful for a narrowly restricted, poorly accessible field of operation, because the instrument and the surgeon's hand do not block the surgeon's view.

In the known microsurgical instrument, a helically turned face is provided on the posterior end of the rotating rod, passing through a transverse slit in a sheath that is axially displaceable by the tappet and is guided in a non-twisting manner. The stationary handle part is disposed in an axial extension of the tube, while the actuating handle part extends parallel to it a small angle away and rests, with a lever bent at right angles, toward the rear of the tappet. The actuating handle part is preferably depressed toward the stationary handle part by the surgeon's thumb.

With this manner of actuation, the surgeon must assume a hand position that is not optimal for highly precise guidance of the microsurgical instrument. Above all, the surgeon cannot, with this kind of actuation, exert great force, as is particularly necessary in applications where the microsurgical instrument is used as a scissors for severing relatively solid tissues, such as cartilage in particular. Finally, the surgeon's hand also prevents an unhindered view of the field of the operation when the instrument is actuated in this way.

In the known instrument, the lever arm of the actuating handle part engages the guide tube of the tappet through a longitudinal slit in order to be able to displace the tappet axially. The guide tube of the tappet is thus open in parts, and pieces of tissue, blood or dirt can get into the guide tube. This makes the cleaning and sterilizing of the instrument difficult and labor-intensive. Finally, the known instrument is extremely complicated in structure and thus expensive to manufacture.

OBJECT AND SUMMARY OF THE INVENTION

It is accordingly the object of the invention to create a microsurgical instrument that overcomes the above-discussed disadvantages and, having a simple design, enables actuation with great force being exerted and without blocking the view.

In a microsurgical instrument of the general type described above, this object is attained by the characteristics of the main claim.

Advantageous forms of embodiment and further developments of the invention are disclosed in the dependent claims.

In the instrument according to the invention, the stationary handle part and the actuating handle part are disposed substantially at right angles to the tube, on the anterior end of which the jaw part is mounted. If the surgeon takes the instrument into his hand, the tube and the jaw part are located above his hand, and the entire field of view above the tube is free. The surgeon's hand thus does not hinder his view of the field of the operation.

Embodying the stationary handle part and the actuating handle part in scissors-like fashion furthermore enables the application of greater actuating forces, for instance in order to sever hard and tough tissue, and yet at the same time it is possible to exert the force in a very sensitively graduated manner.

The tappet protrudes axially toward the rear out of the posterior end of the tube, which is extended in sheath-like fashion; the tappet is sealed radially here by a lid. It is possible to attain very accurate sealing of the tappet, which is displaceable only axially and has a circular cross section, at little expense. The sleeve provided with the helical slit, by which means the axial movement of the tappet is converted into the rotational movement of the rotating rod, is thereby sealed off completely tightly from the exterior, so that no contamination that could create problems with respect to the function or to cleaning and sterilization can get in.

The posterior, outward end of the tappet is fixed on the free, shorter lever arm of the actuating handle part in such a manner that twisting of the tappet is precluded. A certain displaceability between the end of the tappet and the actuating handle part in the longitudinal direction of the actuating handle part must, however, be present as a result of the pivoting motion of the latter. To this end, a longitudinal slit having parallel side faces is preferably provided in the free lever arm of the actuating handle part, and faces of the tappet, correspondingly machined to be parallel, are guided in this slit. As a result, the tappet is held in a non-twisting manner, but it is capable of displacement in the direction of the longitudinal slit relative to the lever arm of the actuating handle part. A restoring element is suitably provided as well on the posterior end of the tappet, enabling a retraction of the tappet as well by means of the actuating handle part. This element is preferably a ball attached to the end of the tappet, the ball being guided in a blind bore in the longitudinal direction of the lever arm of the actuating handle part. The wall of the blind bore is perforated by the longitudinal slit, so that the tappet can be introduced from above, with its plane-parallel faces and the ball disposed on its end, into the free lever arm of the actuating handle part.

The slit of the sleeve, by way of which the axial movement of the tappet is converted into the rotational movement of the rotating rod, may be adapted both in the direction of its helix and in its slope to given conditions for use. For instance, if the microsurgical instrument is intended as a scissors for severing resistant tissue such as cartilage, then the slit is preferably embodied with a relatively flat slope at first, in its more posterior portion, while in the anterior portion the slope increases greatly. As a result, a rapid closure of the cutting jaw parts is attained initially, where the distance the actuating handle part moves is short and there is accordingly little axial displacement of the tappet. In the final portion of the closing movement, when the actual cutting process begins, however, high torque and thus great cutting force by the cutting jaw parts are attained as a result of the steep slope, with a greater axial displacement of the tappet.

The invention will now be described in detail in terms of an exemplary embodiment as shown in the drawing.

BRIEF DESCRIPTION OF THE DRAWING

FIG. 1 shows a microsurgical instrument according to the invention in a lateral view that is partially cut away axially; and FIG. 2 is a partial view of this instrument on a scale enlarged by 2 : 1.

DESCRIPTION OF THE PREFERRED EMBODIMENT

The microsurgical instrument shown in the drawing is embodied as a scissors.

A tubular sheath 10 is attached, preferably by soldering, to a stationary handle part 1, with its axis extending substantially at right angles to this handle part 1. On its anterior end, the sheath 10 has a reduced diameter, in which an elongated tube 12 is inserted coaxially and fixed by means of a pointed screw 9 threaded radially into the sheath 10. A stationary jaw part 15, which in the present case is provided with a cutting edge, is attached to the anterior end of the elongated tube 12.

A rotating rod 13 is supported coaxially and rotatably in the tube 12, and a rotatable jaw part 14 is attached to its anterior end. The rotatable jaw part 14 cooperates with the stationary jaw part 15 and in the present case carries the counterpart cutting edge.

A sleeve 8 is supported coaxially rotatably in the sheath 10, and the rotating rod 13 is inserted in a non-twisting manner, in particular by soldering, into the anterior end face of this sleeve 8. A helical slit 19 is provided in the jacket face of the sleeve 8, extending over virtually the entire length of the sleeve 8.

A tappet 6 is coaxially displaceable in the sleeve 8 and in the vicinity of its anterior end has a radial pin 7, which engages the slit 19 of the sleeve 8. A lid 11 is provided on the posterior end of the sheath 10, having a central bore through which the tappet 6 is guided such that it slides coaxially but in a sealed manner. The lid 11 thus tightly seals both the sheath 10 and the sleeve 8.

An actuating handle part 2 is pivotably articulated on the stationary handle part 1 about a pivot point 4. The stationary handle part 1 and the actuating handle part 2 are embodied in scissors-like fashion; that is, they have relatively long lever arms, which are grasped by the surgeon's hand, while only relatively short, free lever arms project outward beyond the pivot point 4. While the sheath 10 is secured with the tube 12 on the short lever arm of the stationary handle part 1, as already noted, the short, free lever arm of the actuating handle part 2 engages the posterior end of the tappet 6, which protrudes axially out of the lid 11.

This posterior end of the tappet 6 is embodied as a ball 5. Directly before the ball 5 in the axial direction, two plane-parallel and axially parallel faces 16 are milled on the tappet 6. A blind bore 18 is let into the end of the short, free lever arm of the actuating handle part 2 in the longitudinal direction. A longitudinal slit 17 with parallel side walls is milled into the lever arm of the actuating handle part 2, oriented toward the sheath 10; the width of this slit 17 corresponds to the distance between the plane-parallel faces 16 of the tappet 6. The longitudinal slit 17 opens into the blind bore 18 and corresponds in length to it. The posterior end of the tappet 6 is attached to the free lever arm of the actuating handle part 2 by introducing the ball 5 into the blind bore 18 from above, whereupon the plane-parallel faces 16 of the tappet slide within the longitudinal slit 17. In this manner, the tappet 6 can be pushed back and forth axially in the sleeve 8 by means of the actuating handle part 2, in the course of which the tappet is held in a nontwisting manner as a result of the guidance of the faces 16 in the longitudinal slit 17. During this axial movement of the tappet 6, the sleeve 8 and thus the rotating rod 13 as well are set into rotation by means of the radial pin 7. A leaf spring 3 is inserted between the stationary handle part 1 and the actuating handle part 2, its tension being adjustable by a screw. The leaf spring 3 serves to restore the actuating handle part 2 to the position shown by solid lines in FIG. 1, with the tappet 6 being retracted.

The tube 12 bearing the stationary jaw part 15 is turned in the sheath 10 during assembly and positionally fixed by means of the pointed screw 9 such that the stationary jaw part 15 and thus the cutting edge has the desired angular position with respect to the handle parts 1 and 2.

What is claimed is:

1. A microsurgical instrument having a stationary jaw part that is connected via a tube with a stationary handle part, and having a jaw part that is rotatable toward the stationary jaw part, the rotatable jaw part being provided on a rotating rod rotatably and coaxially supported in the tube, wherein the posterior end of the rotating rod is connected with an axially continuous, helical inclined curve with which a tappet is in engagement, the tappet being axially displaceable in a non-twisting manner by means of an actuating handle part articulated such that it is pivotable on the stationary handle part, characterized in that the inclined curve is embodied as a slit of a sleeve coaxially receiving the tappet and rotatably supported in the posterior end of the tube, that the slit is engaged by a radial pin of the tappet, that the stationary handle part and the actuating handle part are disposed substantially at right angles to the tube, that the actuating handle part is articulated in scissor-like fashion on the stationary handle part, its shorter, free lever arm extending behind the posterior end of the tube, and that the posterior end of the tappet is attached in a nontwisting manner on the free lever arm of the actuating handle part and is displacable in the longitudinal direction of the actuating handle part.

2. An instrument as defined by claim 1, characterized in that the tappet is guided in a non-twisting manner with faces parallel to one another and to its axis in a longitudinal slit of the free lever arm of the actuating handle part.

3. An instrument as defined by claim 1, characterized in that a restoring part is provided at the posterior end of the tappet, which restoring part is displacably guided in the free lever art of the actuating handle part on the longitudinal direction thereof.

4. A microsurgical instrument having a stationary jaw part that is connected via a tube with a stationary handle part, and having a jaw part that is rotatable toward the stationary jaw part, the rotatable jaw part being provided on a rotating rod rotatably and coaxially supported in the tube, wherein the posterior end of the rotating rod is connected with an axially continuous, helical inclined curve with which a tappet is in engagement, the tappet being axially displaceable in a non-twisting manner with faces parallel to one another and to its axis in a longitudinal slit of a free lever arm of an activating handle part, the actuating handle part articulated such that it is pivotable on the stationary handle part, characterized in that the inclined curve is embodied as a slit of a sleeve coaxially receiving the tappet and rotatably supported in the posterior end of the tube, that the slit is engaged by a radial pin of the tappet, that the stationary handle part and the actuating handle part are disposed substantially at right angles to the tube, that the actuating handle part is articulated in scissor-like fashion on the stationary handle part, its shorter, free lever arm extending behind the posterior end of the tube, that the posterior end of the tappet is attached in a nontwisting manner on the free lever arm of the actuating handle part and is displaceable in the longitudinal direction of the actuating handle part, and that a restoring part comprises a ball provided on the end of the tappet, which ball is guided in a blind bore of the free lever arm of the actuating handle part, the wall of the blind bore being perforated by the longitudinal slit.

5. An instrument as defined by claim 1, characterized in that the posterior end of the tube is embodied as a sheath, which receives the sleeve and is sealed off from the tappet at its posterior end.

6. An instrument as defined by claim 5, characterized in that the tube and the sheath are rotatable counter to one another and are positionally fixable against one another in a non-twisting manner in any arbitrary rotational position.

7. An instrument as defined by claim 1, characterized in that the inclination of the slit of the sleeve increases in the direction of its anterior end.

8. An instrument as defined by claim 2, characterized in that a restoring part is provided at the posterior end of the tappet, which restoring part is displaceably guided in the free lever art of the actuating handle part in the longitudinal direction thereof.

9. A microsurgical instrument having a stationary jaw part that is connected via a tube with a stationary handle part, and having a jaw part that is rotatable toward the stationary jaw part, the rotatable jaw part being provided on a rotating rod rotatably and coaxially supported in the tube, wherein the posterior end of the rotating rod is connected with an axially continuous, helical inclined curve with which a tappet is in engagement, the tappet being axially displaceable in a non-twisting manner by means of an actuating handle part articulated such that it is pivotable on the stationary handle part, characterized in that the inclined curve is embodied as a slit of a sleeve coaxially receiving the tappet and rotatably supported in the posterior end of the tube, that a restoring part is provided at the posterior end of the tappet, which restoring part is displaceably guided in the free lever arm of the actuating handle part in the longitudinal direction thereof, that the slit is engaged by a radial pin of the tappet, that the stationary handle part and the actuating handle part are disposed substantially at right angles to the tube, that the actuating handle part is articulated in scissor-like fashion on the stationary handle part, its shorter, free lever arm extending behind the posterior end of the tube, that the posterior end of the tappet is attached in a non-twisting manner on the free lever arm of the actuating handle part and is displaceable in the longitudinal direction of the actuating handle part, and that the restoring part comprises a ball provided on the end of the tappet, which ball is guided in a blind bore of the free lever arm of the actuating handle part, the wall of the blind bore being perforated by the longitudinal slit.

10. An instrument as defined by claim 2, characterized in that the posterior end of the tube is embodied as a sheath, which receives the sleeve and is sealed off from the tappet at the posterior end.

11. An instrument as defined by claim 3, characterized in that the posterior end of the tube is embodied as a sheath, which receives the sleeve and is sealed off from the tappet at the posterior end.

12. An instrument as defined by claim 4, characterized in that the posterior end of the tube is embodied as a sheath, which receives the sleeve and is sealed off from the tappet at the posterior end.

13. An instrument as defined by claim 10, characterized in that the tube and the sheath are rotatable counter to one another and are positionally fixable against one another in a non-twisting manner in any arbitrary rotational position.

14. An instrument as defined by claim 11, characterized in that the tube and the sheath are rotatable counter to one another and are positionally fixable against one another in a non-twisting manner in any arbitrary rotational position.

15. An instrument as defined by claim 12, characterized in that the tube and the sheath are rotatable counter to one another and are positionally fixable against one another in a non-twisting manner in any arbitrary rotational position.

16. An instrument as defined by claim 2, characterized in that the inclination of the slit of the sleeve increases in the direction of its anterior end.

17. An instrument as defined by claim 3, characterized in that the inclination of the slit of the sleeve increases in the direction of its anterior end.

18. An instrument as defined by claim 4, characterized in that the inclination of the slit of the sleeve increases in the direction of its anterior end.

19. An instrument as defined by claim 5, characterized in that the inclination of the slit of the sleeve increases in the direction of its anterior end.

20. An instrument as defined by claim 6, characterized in that the inclination of the slit of the sleeve increases in the direction of its anterior end.

* * * * *